(12) United States Patent
Fishman et al.

(10) Patent No.: US 6,939,378 B2
(45) Date of Patent: Sep. 6, 2005

(54) MICROFABRICATED TISSUE AS A SUBSTRATE FOR PIGMENT EPITHELIUM TRANSPLANTATION

(75) Inventors: Harvey A. Fishman, Menlo Park, CA (US); Mark Blumenkranz, Portola Valley, CA (US); Stacey Francine Bent, Palo Alto, CA (US); Christina Lee, San Francisco, CA (US); Philip Huie, Jr., Cupertino, CA (US); Daniel V. Palanker, Sunnyvale, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 426 days.

(21) Appl. No.: 09/872,513

(22) Filed: Jun. 1, 2001

(65) Prior Publication Data

US 2002/0183844 A1 Dec. 5, 2002

(51) Int. Cl.$^7$ .................................................. A61F 2/14
(52) U.S. Cl. ........................ 623/4.1; 623/6.63; 623/2.16
(58) Field of Search ................................ 623/6.63, 4.1; 424/93.7

(56) References Cited

U.S. PATENT DOCUMENTS

| 5,962,027 A | 10/1999 | Hughes |
| 6,045,791 A | 4/2000 | Liu |

OTHER PUBLICATIONS

L. Lu, et al., "Retinal pigment epithelium cell culture on thin biodegradable poly(DL–lactic–co–glycolic acid) films", J. Biomater Science Edn. vol. 9, No. 11 pp. 1187–1205 (1998).

T. Dintelmann, et al., "Comparative study of ROS degradation by IPE and RPE cells in vitro", Graefe's Arch Clin. Exp. Ophthalmology 1999 No. 237 pp 830–839.

C.D. James, et al., "Aligned Microcontact Printing of Micrometer–Scale Poly–L–Lysine Structures for Controlled Growth of Cultured Neurons on Planar Microelectrode Arrays", IEEE Transaction On Biomedical Engineering, vol. 47, No. 1, Jan. 200, pp 17–21.

U. Hartmann, et al., "Human and porcine anterior lens capsule as support for growing and grafting retinal pigment epithelium and iris pigment epithelium", Graefe's Arch Clin Exp Ophthalmoloy (1999), vol. 237, pp 940–945.

G. Thumann, et al., Transplantation of Autologous Iris Pigment Epithelium After Removal of Choroidal Neovascular Membranes, Arch Ophthalomology (Oct. 2000), vol. 118, pp. 1350–1355.

L. Lu, et al., "Retinal pigment epithelial cell function on substrates with chemically micropatterned surfaces", Biomaterials (Dec. 1999), vol. 20 No. 23/24, pp. 2351–2361.

(Continued)

Primary Examiner—Corrine McDermott
Assistant Examiner—William H Matthews
(74) Attorney, Agent, or Firm—Lumen Intellectual Property Services, Inc.

(57) ABSTRACT

Methods and apparatus for modifying membranous tissue, growing cells on modified membranous tissue, and for transplantation of modified tissues and modified tissues with attached cells are provided. In particular, the invention provides methods and apparatus for modifying membranous tissue such as lens capsule tissue and inner limiting membrane tissue, for growing cells such as iris pigment epithelial (IPE) cells and retinal pigment epithelial (RPE) cells on modified membranous tissue, and for modifying membranous tissue and growing cells on biodegradable polymer substrates. A method of modifying membranous tissues comprises depositing micropatterns of biomolecules onto membranous tissue with a contacting surface such as a stamp; other methods include mechanical ablation, photoablation, ion beam ablation, and modification of membranous tissues via the action of proteolytic enzymes.

18 Claims, 5 Drawing Sheets

OTHER PUBLICATIONS

A. Lappas, et al., "Cilinical investigation: Iris pigment epithelial cell translocation in exudative age-related mascular degeneration, A pilot study in patients", Graefe's Archive for Clinical Experimental Opthalmology, Abstract, vol. 238 issue, p. 1 and 2 electronic version, ISSN: 1435–702X, http://link.springer-ny.com/link/service/journals/00417/bibs/0238008/02380631.htm.

Giordano, et al., "Retinal pigment epithelium cells cultured on synthetic biodegradable polymers", (Abstract), http://www.ncbi.nlm.nih.gov/entrez/query.fcgi?cmd=Retrieve&db=PubMed&list_uids=897 . . . 6.

Abe T., et al., "Auto iris pigment epithelial cell transplantation in patients with age-related mascular degeneration: short–term results", (Abstract), http://www.n . . . /query-.fcgi?cmd=Retrieve&dblist=PubMed&list_uids=10896035&dopt=Abstrac.

Abe T., et al., "Functional analysis after auto iris pigment epithelial cell transplantation in patients with age-related macular degeneration", (Abstract), http://www.n . . . /query.fcgi?cmd=Retrieve&db=PubMed&list_uids=10739165&dopt=Abstrac.

Nicolini, et al., "The anterior lens capsule used as support material in RPE cell–transplantation", (Abstract), http://www.ncbi.nlm.nih.gov/entrez/query.fcgi?cmd=Retrieve&db=PubMed&list_uids=11C . . . 7.

MICROFABRICATED TISSUE AS A SUBSTRATE FOR PIGMENT EPITHELIUM TRANSPLANTATION

FIELD OF THE INVENTION

The present invention relates generally to the field of treatment of eye disorders, in particular retinal disorders such as age-related macular degeneration, retinitis pigmentosa, and other retinal diseases. In addition, the invention relates to methods and apparatus for modifying tissues, and for the transplantation of cells and tissues.

BACKGROUND OF THE INVENTION

Diseases of the retina, such as age-related macular degeneration (AMD), retinitis pigmentosa (RP), and other diseases, are the leading cause of severe visual impairment or blindness in the industrialized world. One hallmark of AMD, as in RP, is the degeneration and loss of cells of the retinal pigment epithelium (RPE). Bruch's membrane is also thought to be damaged; such damage may be the initiating stimulus for RPE demise. RPE cells are vital to the survival and proper functioning of retinal photoreceptors, which are the only cells in the eye which directly sense light. RPE degeneration in retinal diseases such as AMD and RP is related to the loss of photoreceptor function and the visual impairment that is associated with these diseases.

The RPE is located adjacent to the neural retina, directly opposed to the retinal photoreceptors. RPE cells in vivo form a one cell thick cobblestone-like tissue linked together by tight junctions, with differentiated apical and basal membranes. The RPE cells in vivo grow tightly packed together at high density to form a tight epithelium that acts as a barrier regulating transport between the photoreceptors and the underlying Bruch's membrane, choroid and the choroidal vasculature. The apical portion of the RPE is adapted to surround and engulf photoreceptor outer segments, in order for it to perform its vital functions of phagocytosis and digestion of shed photoreceptor tips, and of recycling retinal for re-use in photopigments. The basal portion of the RPE is apposed to Bruch's membrane, a highly vascularized supporting membrane which supplies the RPE and photoreceptors with needed oxygen and nutrients, and prevents the accumulation of carbon dioxide and other waste products which would otherwise impair retinal function. Damage to Bruch's membrane, which may occur due to accumulation of waste products from outer segment metabolism, for example, prevents the exchange of oxygen, growth factors and waste products. Such impaired exchange leads to hypoxia in the photoreceptors. In response, it is thought that survival signals are sent out to initiate the in-growth of neovascular vessels, and so to the wet form of AMD.

The iris pigment epithelium (IPE), which, like the RPE is derived from the neuroectoderm of the embryo, is located adjacent to the iris at the part of the eye opposite to the retina. Thus, in place in the intact eye, IPE cells are remote from retinal photoreceptors. Although much about IPE cell physiology and function remains unknown, like RPE cells, IPE cells in culture have been shown to be capable of phagocytosis of photoreceptor outer segments.

RPE cells may be grown on artificial substrates (Pfeffer, B. A., Chapter 10, "Improved Methodology for Cell Culture of Human and Monkey Retinal Pigment Epithelium," *Progress in Retinal Research*, Vol. 10 (1991) Ed. Osborn, N., and Chader, J.; Lu et al., *J. Biomater. Sci. Polymer Edn.* 9:1187–1205 (1998), and Lu et al., *Biomaterials* 20:2351–2361 (1999). In addition, there have been attempts to use lens capsule tissue as a substrate for growing RPE and IPE cells (Hartman et al., Graefe's *Archiv Clin Exp Ophthalmol* 237:940–945 (1999); Nicolini et al., *Acta Ophthalmol Scand October,* 2000;78(5):527–31)).

Many approaches have been tried in the treatment of degenerative and progressive retinal diseases. For example, attempted treatments for AMD include photodynamic therapy, radiation therapy, and macular relocation in order to repair, retard the progression, or compensate for the effects of the disease. However, such approaches have not met with great success.

Since RPE cell loss occurs in many retinal diseases, the transplantation of cells has great attraction as a therapy and possible cure for AMD and other diseases. Direct transplantation of RPE cells into the retina has been attempted in order to replace lost RPE cells. However, this approach has not succeeded in the past, due in part to the failure of the transplanted cells to function properly and in part due to rejection of the cells by the host animals.

Transplantation of RPE cells has been suggested as a therapy for retinal dystrophy (U.S. Pat. No. 5,962,027 to Hughes and U.S. Pat. No. 6,045,791 to Liu). All patents named herein, both supra and infra, are hereby incorporated by reference in their entirety. In addition, experimental evidence that IPE cells could substitute for RPE cells has led to preliminary attempts to transplant IPE cells in animals and in order to ameliorate symptoms of AMD (Abe et al., *Tohoku J. Exp. Med.* 189:295–305 (1999), Abe et al., *Cell Transplantation* 8(5):501–10 (1999); Schraermeyer et al., *Invest. Opth. Vis. Sci.* 40(7):1545–56 (1999); Thumann et al., *Transplantation* 68(2)195–201 (1999); Abe et al., *Tohoku J. Exp. Med.* 191:7–20 (2000); Abe et al., *Current Eye Research* 20(4):268–275 (2000); Lappas et al., *Graefes 's Arch Clin Exp Ophthalmol* 238:631–641 (2000), Thumann, et al.,*Arch. Ophthalmol.* 118:1350–1355 (2000)).

However, challenges to both IPE and RPE transplantation methods include i) difficulty in repairing the diseased Bruch's membrane, ii) inability to secure and position newly transplanted cells, and iii) lack of control over extracellular matrix signaling molecules that are critical to the structure, function, and survival of the pigment epithelial cell. For these and other reasons, techniques for IPE and RPE transplantation using antibiotics or immunosuppressants have not been successful. There has been no demonstration of significant visual improvement with these approaches, and problems of tissue reintegration remain. Thus, despite the apparent promise of the transplantation approach, AMD and other retinal diseases remain without successful therapeutic interventions.

Accordingly, there is need in the art for novel methods and apparatus for modification of tissues for transplantation and for transplantation of such tissues for the relief of retinal diseases.

BRIEF SUMMARY OF THE INVENTION

The present invention is directed to methods, apparatus, and related products for modifying tissues and growing cells for transplantation. In particular, the invention is directed towards methods, apparatus, and related products for transplantation of cells and tissues into the retina for treatment of retinal diseases such as AMD and RP. Tissues modified by the novel methods disclosed herein are termed microfabricated tissues. The invention includes microfabricated membranous tissues, including microfabricated ocular membranous tissues, for example microfabricated lens capsule tissues and microfabricated inner limiting membrane tissues. The invention further includes microfabricated membranous tissues for use in transplantation, methods for microfabricating membranous tissues, methods for using microfabricated membranous tissues, methods for growing cells on microfabricated membranous tissues, and methods for transplanting microfabricated tissues and cells into the eye of an animal. For example, the animal may be a human.

Methods for modifying membranous tissues may include mechanical methods including mechanical ablation, mechanical contact, and photoablation methods. The methods of the invention for modifying membranous tissues may be applied to a variety of tissues, including ocular membranous tissues. For example, the methods of the invention include methods for modifying lens capsule tissue, such as human lens capsule tissue, and for modifying inner limiting membrane tissue, such as human inner limiting membrane tissue.

Methods for modifying membranous tissues include bulk modification methods and surface modification methods. Surface modification methods and bulk modification methods may be applied alone, or may each be applied together to the same membranous tissue. Modification of the surface and bulk properties of the membranous tissue improves the tissue's suitability for transplantation into an animal. Such tissue modification may improve the ability of cells to attach and grow on the tissue, and may improve the permeability properties of the tissue so that nutrients, electrolytes, and other desired substances are better able to pass through the modified tissue.

The methods of the invention, whether bulk or surface modification methods, include removal of membranous tissue, such as a lens capsule or an inner limiting membrane, from an eye, flattening the membranous tissue onto a glass or plastic substrate, such as a coverslip, submersed in phosphate buffered saline, or flattening the membranous tissue onto a temporary dissolvable polymer for ease of surgical transplantation. The modified tissue provides a suitable substrate for cells, and may be exposed to cells which may attach and grow. The modified tissue, with adherent cells if any were applied to and grown on the tissue and/or with polymer, if any, may next be transplanted into a desired location within the body of an animal. Following transplantation, where the modified tissue has been prepared with a dissolvable polymer, the polymer will dissolve and be absorbed by the body of the animal into which the tissue has been transplanted, leaving the transplanted tissue and cells in place.

Suitable dissolvable polymers include poly-lactic acid, polyglycolic acid, polyorthoesters, poly anhydrides, polyphosphazines, poly-lactic acid glycolic acid copolymers (PLGA), including PLGA (50:50 lactic to glycolic acid copolymer), poly-lactic acid polymers (PLLA), polyethylene glycol/polylactic acid copolymer (PEG/PLA), and blends and co-polymers thereof.

Bulk modification methods are those where substantial portions of the membranous tissue, not limited to surface portions of the tissue, are modified by the method. Surface modification methods are those where the membranous tissue is modified at and near to the surface, but is not greatly modified in other portions of the tissue.

Bulk modification methods for modifying membranous tissue, including ocular membranous tissue such as lens capsule tissue and inner limiting membrane tissue, include methods for modifying the thickness, permeability, and other properties of the tissue. Bulk modification methods include mechanical ablation, including rubbing, scraping, cutting, and applying tension, contacting the membranous tissue with a contacting surface such as a stamp, and producing a micropattern in the membranous tissue. In one embodiment of the bulk modification method, treatment after removal and flattening of the membranous tissue includes use of a laser or ion beam to modify the surface of the membranous tissue to reduce the overall thickness of the tissue. For example, the lens capsule, which can normally be up to about 8 to 14 $\mu$m thick, may be ablated by photoablation with an excimer laser to be about 2 to 5 $\mu$m thick, so that the overall thickness of the altered lens capsule mimics the thickness of Bruch's membrane (about 2 to 4 $\mu$m).

In another embodiment of the bulk modification method, such further treatment includes photoablation using a laser, such as an excimer, titanium sapphire, or YAG laser, or ion beam treatment, to produce micropores or pits in the membranous tissue. The micropores may be sized on the order of a few micrometers or less in diameter. A micropattern of micropores or pits produced in the membranous tissue by such treatment.

Membranous tissue may be treated by impregnation with a deactivated collagenase enzyme that is activated by laser light illumination. For example, very small regions sized less than a micrometer in diameter of tissue may be activated by illumination with a 2-photon confocal laser system.

Enzymes may be deposited onto the membranous tissue effective to biologically etch the surface and interior of the membranous tissue effective to provide desired topology and surface adhesion properties to the tissue. In some embodiments of this method, the deposition step includes contacting the membranous tissue with a contacting surface, such as a microcontact printing stamp, carrying enzymes effective to biologically etch the surface and interior of the membranous tissue.

Treatments may include surface modification of the membranous tissue as well. For example, treatment may include deposition of patterns of biomolecules onto membranous tissue, and production of patterns of pores or pits or other surface features by laser or ion beam treatment. In some embodiments of this method, the patterns are sized on the order of a few micrometers or less. In other embodiments of this method, the biomolecules include peptides and small chain polymers effective to deactivate selective cell attachment sites on membranous tissue.

In one embodiment of the surface modification method, microcontact printing techniques are used to fabricate chemical micropatterns of biomolecules on the membranous tissue. Membrane surfaces may also be modified by mechanical ablation methods including rubbing, scraping and flowing solutions over the surface.

In another embodiment of the surface modification method, the surface of the membranous tissue is masked to cover part, but not all, of the surface of the tissue, and then irradiated with ultraviolet (UV) radiation effective to denature the extracellular matrix (ECM) of the exposed portions of tissue. In order to activate only certain portions of the surface of the membranous tissue, a deactivating substance such as polyvinyl alcohol (PVA) or mucilage can be applied to the surface of the tissue, and an excimer laser can be used to ablate a micropattern on the membranous tissue surface through an irradiation mask.

The masking step may be performed by placing a grid onto the surface of the membranous tissue, or by using microcontact printing techniques to apply a pattern of protecting molecules onto the surface of the membranous tissue effective to prevent ECM denaturation in regions covered by the protecting molecules or grid.

Cells may be grown on microfabricated membranous tissues. For example, cells may be applied to microfabricated membranous tissues which may have patterns on their surfaces. In further embodiments, the microfabricated membranous tissue may be lens capsule tissue or inner limiting membrane tissue, and the cells may be IPE cells. In yet other embodiments of the invention, the microfabricated membranous tissues and the cells may be obtained from the same animal. In this last case, transplantation of the modified tissue and cells into that animal would be autologous transplantation, which would not suffer from rejection by the animal's immune system.

The invention also provides methods for using microfabricated membranous tissues, including surgical methods for transplanting microfabricated membranous tissues into an animal. The methods for transplanting microfabricated membranous tissues into an animal include surgical methods for transplanting microfabricated membranous tissues into the eye of an animal, such as transplantation of microfabricated lens capsule tissue or microfabricated inner limiting membrane tissue near to or into the retina of an animal. The transplanted tissue may further include cells grown on microfabricated lens capsule tissues or microfabricated inner limiting membrane tissues. In preferred embodiments, the transplanted microfabricated membranous tissue includes IPE cells grown on microfabricated lens capsule tissues or microfabricated inner limiting membrane tissues, and may be autologous tissue and cell transplants.

The invention also provides products useful in fabricating and using microfabricated tissues. Such products include products and tools for making modified ocular membranous tissues, including microfabricated lens capsule and inner limiting membrane tissues, and products and tools for transplanting the transplanted tissues and cells into the eye of an animal.

The present invention is directed to methods and related products for treating retinal diseases such as AMD, RP, and other retinal diseases. For example, one therapy for AMD is to transplant suspensions of either retinal pigment epithelial (RPE) cells or iris pigment epithelial (IPE) cells to rescue the diseased retina. The present invention provides novel tissue engineering techniques to precision engineer autologous human tissues (e.g., human lens capsule) as a substrate for transplanting cells, such as IPE and RPE cells. Transplanted pigment epithelium cells grown on the modified tissue and substrates of the invention are able to grow to high density and to exhibit features indicative of differentiation, important characteristics of these cells in normal retinas. In addition, unlike prior methods, the modified membranous tissues (including modified ocular membranous tissues, such as lens capsule, inner limiting membrane, and other substrates provided by the present invention, and such substrates with growing epithelial cells) are effective to replace many of the functions of Bruch's membrane, which may be damaged in degenerative retinal diseases. Thus the present methods and apparatus for transplantation of pigment epithelial cells provide transplanted cells which grow to high density and are able to perform needed physiological functions lacking in patients with retinal degenerative diseases.

DETAILED DESCRIPTION OF THE INVENTION

Figure 1A:
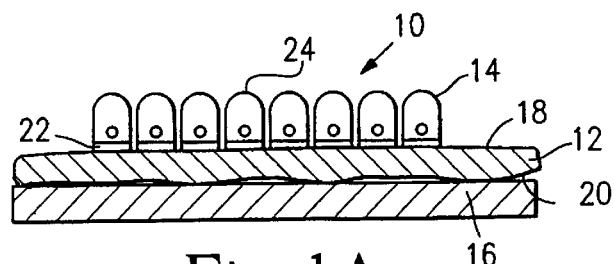
FIG. 1A is a cross-sectional view of microfabricated membranous tissue on a dissolvable substrate embodying features of the invention.

The present invention provides methods and apparatus for modifying tissues and cells for transplantation. The methods of the invention for modifying tissues may be applied to a variety of tissues from a variety of organs. The following definitions are helpful in describing the invention.

The term "autologous" is used herein to refer to cells or tissues derived from the same animal as other cells or tissues; thus, with respect to a tissue, cells are autologous cells when they are derived from the same animal as the tissue is derived from; analogously, the tissue is autologous tissue with respect to the cells when the cells and tissue are derived from the same animal.

The term "biomolecule" is used herein to mean a molecule that has a biological activity. Thus, a biomolecule is one that, when in contact with a cell or tissue, acts on or affects that cell or tissue.

The term "bulk modification" is used herein to mean the modification of the properties of substantial portions of a tissue, where such modification is not limited to the surface portions of the tissue.

The term "surface modification" is used herein to mean the modification of the properties of a tissue at and near to the surface of the tissue.

The term "membranous tissue" is used herein to mean any tissue of an animal that forms a sheet or sheath; membranous tissue commonly encloses or delimits a tissue, or divides an organ or tissue into separate compartments. "Ocular membranous tissue" is used herein to mean membranous tissue derived from the eye of an animal; lens capsule tissue and inner limiting membrane are examples of ocular membranous tissue, as are corneal membranes, Bruch's membrane, and other membranous tissues of the eye.

The term "ablation" is used herein to mean the alteration of a tissue, not necessarily including the reduction in the size or the removal of tissue. As used herein, "mechanical ablation" means alteration, reduction, or removal of tissue by mechanical action, such as scraping, scoring, contacting with a contacting surface (such as a stamp), applying tension, or other mechanical method. As used herein, "photoablation" means irradiation by ultraviolet light, laser light, or other radiation, such as by light from an excimer, titanium sapphire, YAG or other laser, effective to alter the surface or bulk properties of a tissue. "Ion ablation" is used herein to refer to surface or bulk modification effected by ion beam treatment of a membranous tissue.

A "proteolytic enzyme," or a "protease," is a type of molecule that is effective to at least partially digest (cut into pieces) a protein or peptide molecule. Examples of proteases and proteolytic enzymes include, but are not limited to, collagenase, trypsin, chymotryptsin, dispase, liberase, thermolysin, pepsin, and papain.

The term "transplantation" is used herein to mean the insertion, deposition or positioning of cells or tissues into an animal. The deposition of cells growing on modified lens capsule tissue into the subretinal space is an example of transplantation.

The term "microcontact printing" is used herein to mean deposition of desired molecules onto a surface in a pattern with features sized on the order of several tens of microns or smaller.

The term "microfabrication" is used herein to mean the production of modified tissues by surface modification, bulk modification, or both.

The term "microfabricated tissue" is used herein to mean a tissue that has been altered or modified by microfabrication methods.

A "contacting surface" is a surface configured for contacting a second surface and for depositing molecules initially present on the contacting surface onto the second surface. A "stamp," "microfabrication stamp," "microcontact printing stamp," "microcontact stamp," or "microfabrication printing stamp" is a contacting surface, and the terms "stamp," "microfabrication stamp," "microcontact printing stamp," "microcontact stamp," and "microfabrication printing stamp" are used herein to mean a device adapted to deposit desired molecules in a pattern with features sized on the order of several tens of microns or smaller.

The term "micropattern" is used herein to mean a pattern, such as an ordered array, design or contour with features sized on the order of several tens of microns or smaller.

By "dissolvable polymer" is meant a polymer that is biodegradable, and that upon introduction into an animal may at least partially dissociate and disperse into fluids and tissues of the animal.

A "laser" may be an excimer laser, a titanium sapphire laser, an yttrium-aluminum-garnet (YAG), or other laser. A laser is capable of emitting a powerful beam of coherent light produced by light amplification within the laser cavity or crystal of the laser.

As used herein "excimer laser" means a laser light source that provides laser light of a wavelength below about 400 nm. Excimer lasers may be xenon, krypton, or fluorine lasers, or, more preferably may be an argon fluoride laser. An argon fluoride laser provides laser light in the ultraviolet, typically with a wavelength of about 193 nm, suitable for ablation of epithelial, connective, and other tissues. For use in tissue modification, such as tissue ablation, laser light may be pulsed at between about 1 to 50 Hz with each pulse having a duration of between about 1 to 200 ns, preferably between about 10 to 20 ns. Laser beams, such as produced by argon fluoride lasers, are typically sized on the order of a few millimeters to several tens of millimeters.

A titanium-sapphire (TiS) laser is a tunable laser capable of emiting infrared laser light with wavelengths ranging from about 700 to about 1100 nm.

An yttrium-aluminum-garnet (YAG) laser, such as a neodimium YAG, a horonium YAG, or an erbium YAG laser, is a solid-state laser emitting laser light at a wavelength on the order of a micron. Water molecules absorb energy at micron wavelengths; water preferentially absorbs energy at wavelengths near 3 microns, and erbium-doped YAG lasers emit light with a wavelength of 2.94 microns, making them particularly suitable for use in photoablation by rapid, local vaporization of water present in cells and tissues, causing rapid expansion and ablation of tissue.

An ion beam is a beam of ionized gas molecules, typically excited by radio-frequency energy and directed at a target. Ion beam sources used in the practice of the present invention may be of any kind; an ion beam source is described, for example, in U.S. Pat. No. 5,216,330 to Ahonen. Ion beams may be used to create holes in materials. U.S. Pat. No. 6,093,445 to Nawate describes an ion beam method for producing rectangular and circular holes sized from about 10 nm to about 2 $\mu$m.

A tissue implant 10 having microfabricated lens capsule tissue 12 with attached cells 14 and a dissolvable substrate 16 is shown in cross-section in FIG. 1A. Cells 14 are attached to and growing upon upper surface 18 of the microfabricated lens capsule tissue 12. Lower surface 20 of the microfabricated lens capsule tissue 12 is in contact with the dissolvable substrate 16. Cells 14 are iris pigment epithelial cells, which have apical 22 and basal 24 membranes, with basal membranes 22 in contact with upper surface 18 of the microfabricated lens capsule 12. Expression of the proper cellular differentiation into basal 22 and apical 24 membranes, as is found in pigment epithelial cells in vivo, is indicative of the proper functioning of the epithelial cells growing on the microfabricated lens capsule.

Figure 1B:
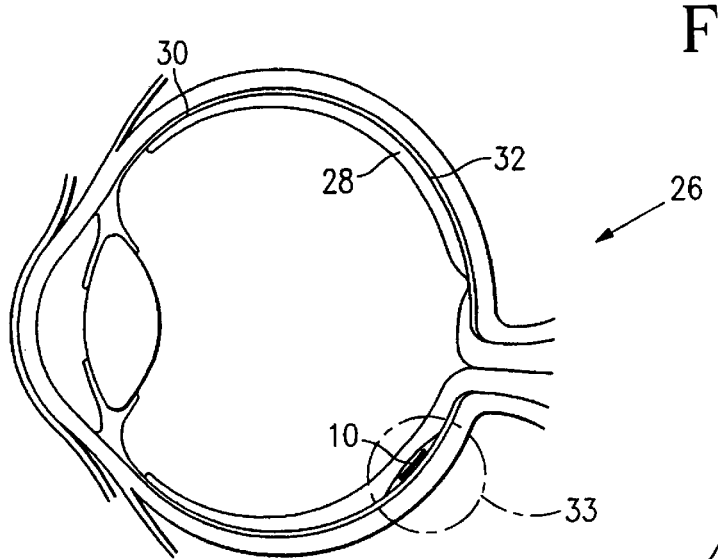
FIG. 1B is a cross-sectional view of an eye of an animal having microfabricated tissue on a dissolvable substrate implanted in the subretinal space of its eye.
Figure 1C:
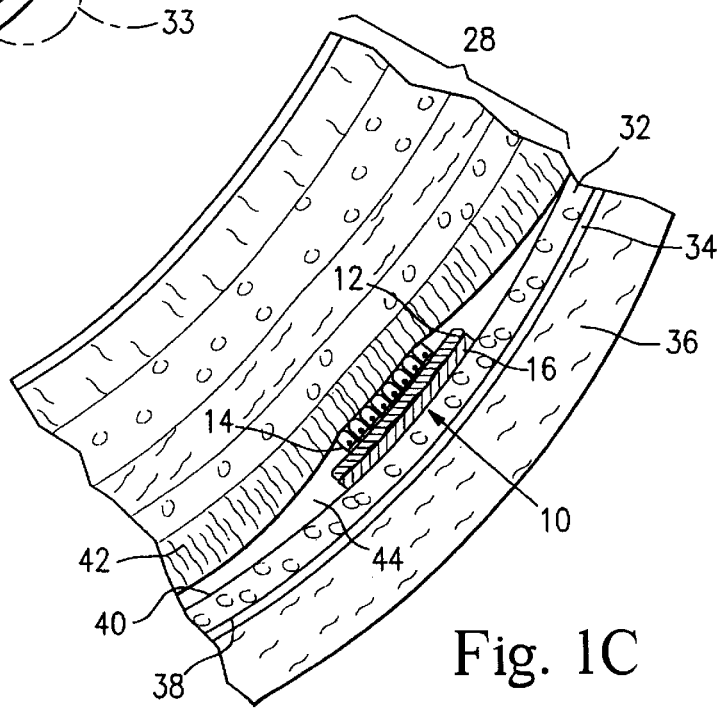
FIG. 1C is a detailed cross-sectional view of the microfabricated tissue, retina and subretinal space of the eye shown in FIG. 1.

FIG. 1B illustrates, in cross-section, an eye 26 of a mammalian animal into which the tissue implant 10 has been surgically placed. FIG. 1C is a detail of the region within circle 33 of eye 26 including neural retina 28 and tissue implant 10. Shown in FIGS. 1B and 1C are the neural retina 28, the iris pigment epithelium (IPE) 30, the retinal pigment epithelium (RPE) 32 growing on Bruch's membrane 34 which separates the choroid 36 from the basal membrane 38 of the RPE. The apical membrane 40 of the RPE has numerous processes which enfold and surround the light-sensitive portions of the photoreceptors in the photoreceptor layer 42 of the neural retina 28. The space between the apical membranes of the RPE 40 and the photoreceptors 42 is the subretinal space 44. The choroid 36 serves to maintain an environment capable of supporting the high metabolic demands of the photoreceptor layer 42 in particular and the neural retina 28 in general by allowing the passage of nutrients and electrolytes to, and removal of waste products from, the subretinal space 44.

In a healthy eye, the subretinal space 44 is only a virtual space, there being only minimal separation between photoreceptors 42 and apical portions of the RPE 40. However, in many eye disorders, such as retinal detachment, the photoreceptors 42 may become separated from the apical RPE membranes 40. In addition, the neural retina 28 and the pigment epithelium 30 and 32 may be artificially separated during eye surgery if desired. As shown in FIGS. 1B and 1C, a tissue implant 10 may be placed into the subretinal space 44. Microfabricated lens capsule 12 with adherent IPE cells 14 is shown implanted into eye 26 where the IPE cells 30 are able to contact photoreceptors 42 and provide metabolic support. Dissolvable substrate 16 is shown between the lower surface 20 of the microfabricated lens capsule 12 and the choroid 36, as it is initially after placement of the tissue implant 10. However, the dissolvable substrate 16 will dissolve and be removed from the subretinal space 44 leaving only the transplanted microfabricated lens capsule 12 and attached IPE cells 14 in place in the subretinal space 44.

Figure 2:
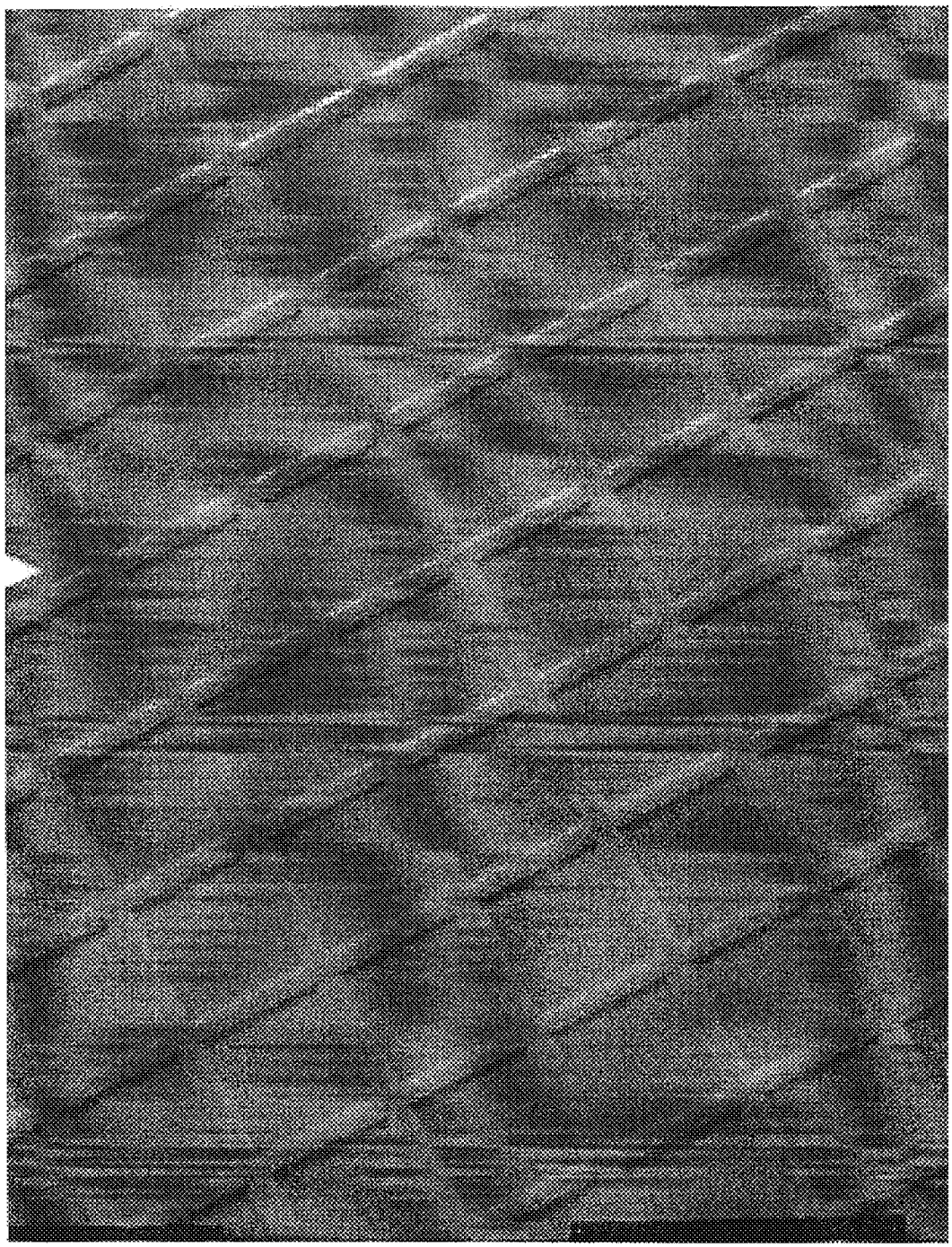
FIG. 2 illustrates a microcontact printing stamp useful for producing microfabricated membranous tissue embodying features of the invention.

FIG. 2 is a scanning electron micrograph (SEM) of a poly(dimethylsiloxane) (PDMS) microfabrication stamp embodying features of the invention. The grid-lines are separated by about 50 µm. Grid lines may be coated with compounds, for example, poly-L-lysine, for placement onto a surface by contacting the surface with the stamp.

Figure 3:
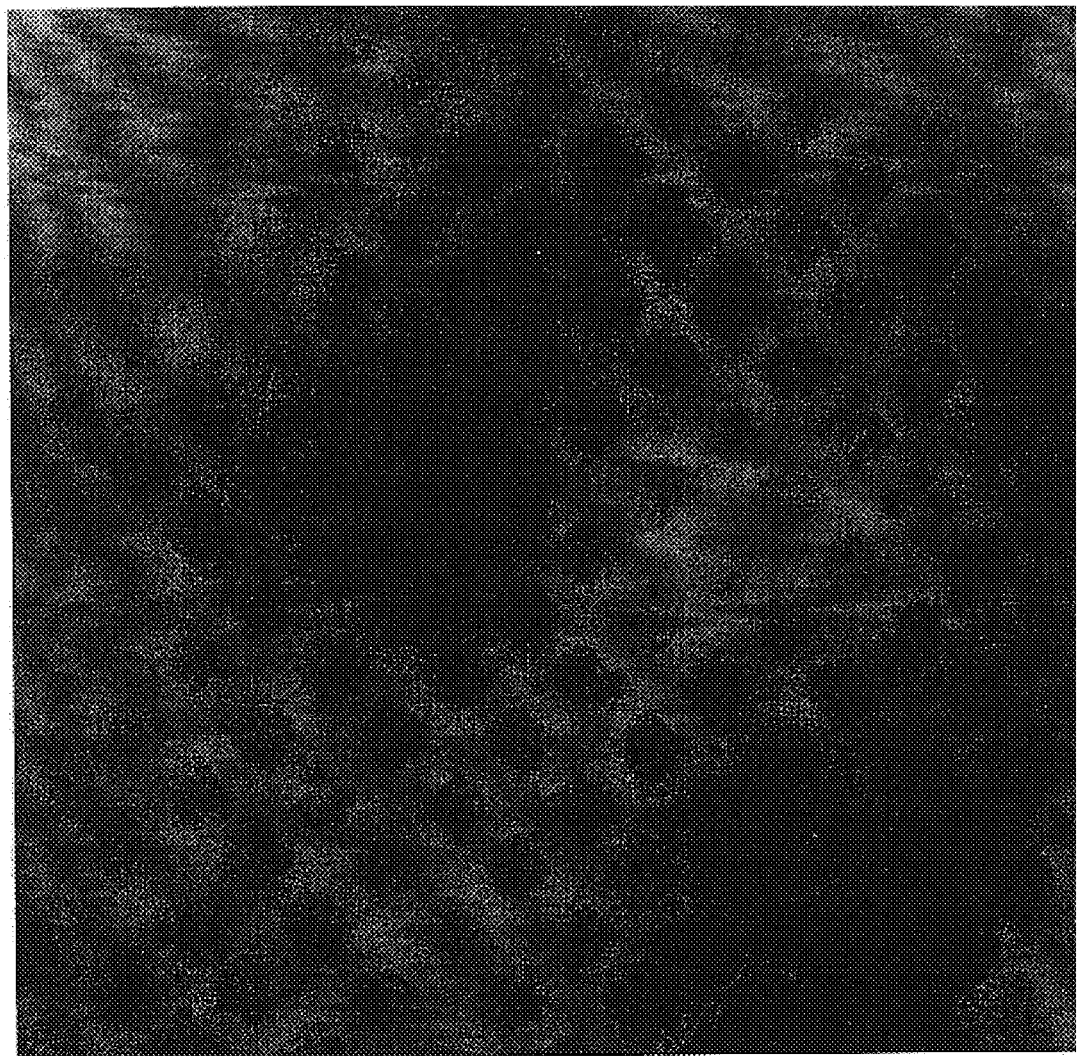
FIG. 3 illustrates microfabricated lens capsule tissue after contact with a microcontact printing stamp embodying features of the invention.

FIG. 3 is a SEM of a microfabricated lens capsule tissue after contact with the microfabrication stamp shown in FIG. 2 that had been coated with poly-L-lysine. Micropattern lines follow the same pattern and spacing as the stamp that produced them by contact with the lens capsule surface.

Figure 4:
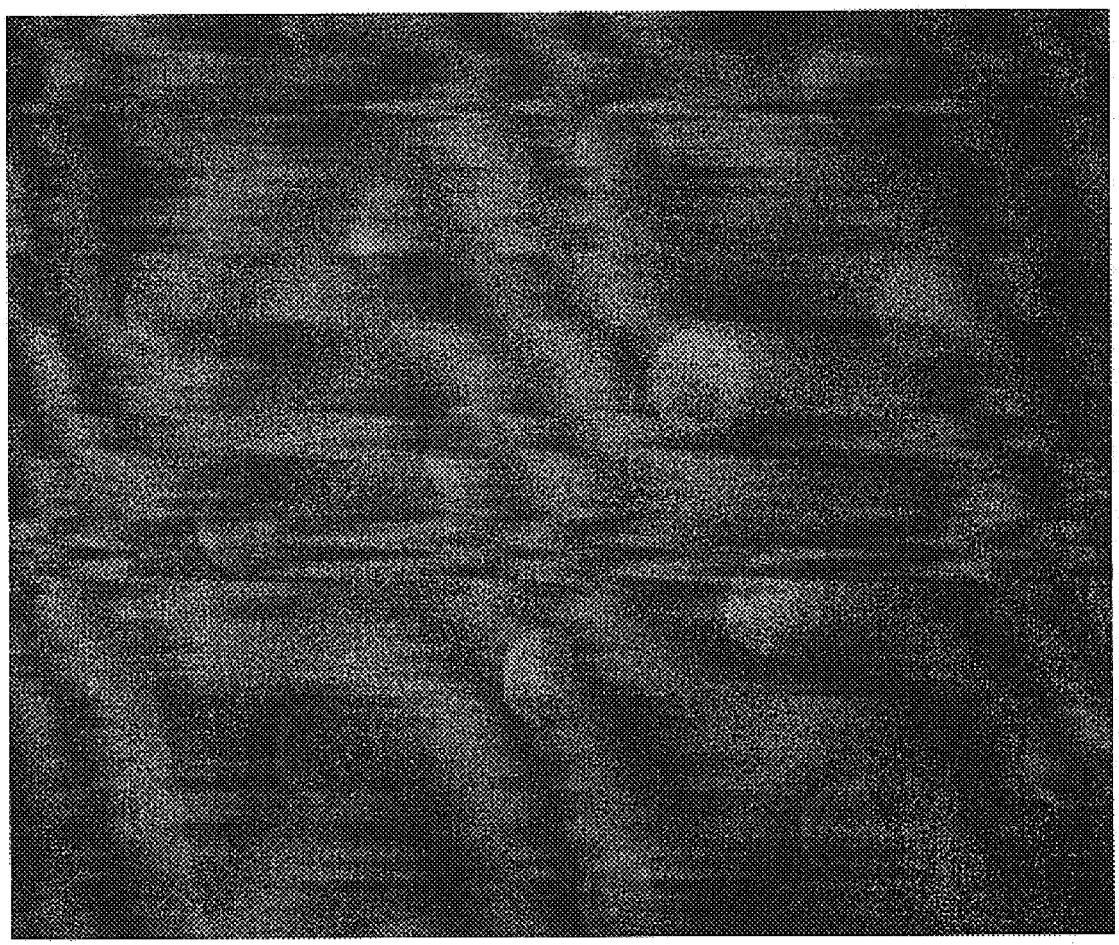
FIG. 4 illustrates a PDMS stamp for micropatterning membranous tissue according to methods embodying features of the invention.

FIG. 4 shows a SEM of a PDMS stamp that has a stamp surface with a topology given by an array of circular wells. Thus, the stamp surface of stamp has circular depressions that will not receive a coating while the rest of the stamp surface does receive a coating of molecules which may then be transferred to any surface with which it becomes in contact. Coating the stamp with molecules, such as polyvinyl alcohol (PVA), mucilage, or other inhibitory molecules, and then placing the stamp in contact with a surface, such as a lens capsule surface, leaves a pattern of those molecules on the surface everywhere but on the circles themselves. Such a micropattern of inhibitory molecules allows cells growing on the surface to attach only on these circular areas. Because the unmodified lens capsule surface actively allows growth of cells adherent to it, inhibitory patterns are required for patterned growth. Each circle is about 50 µm in diameter.

Figure 5:
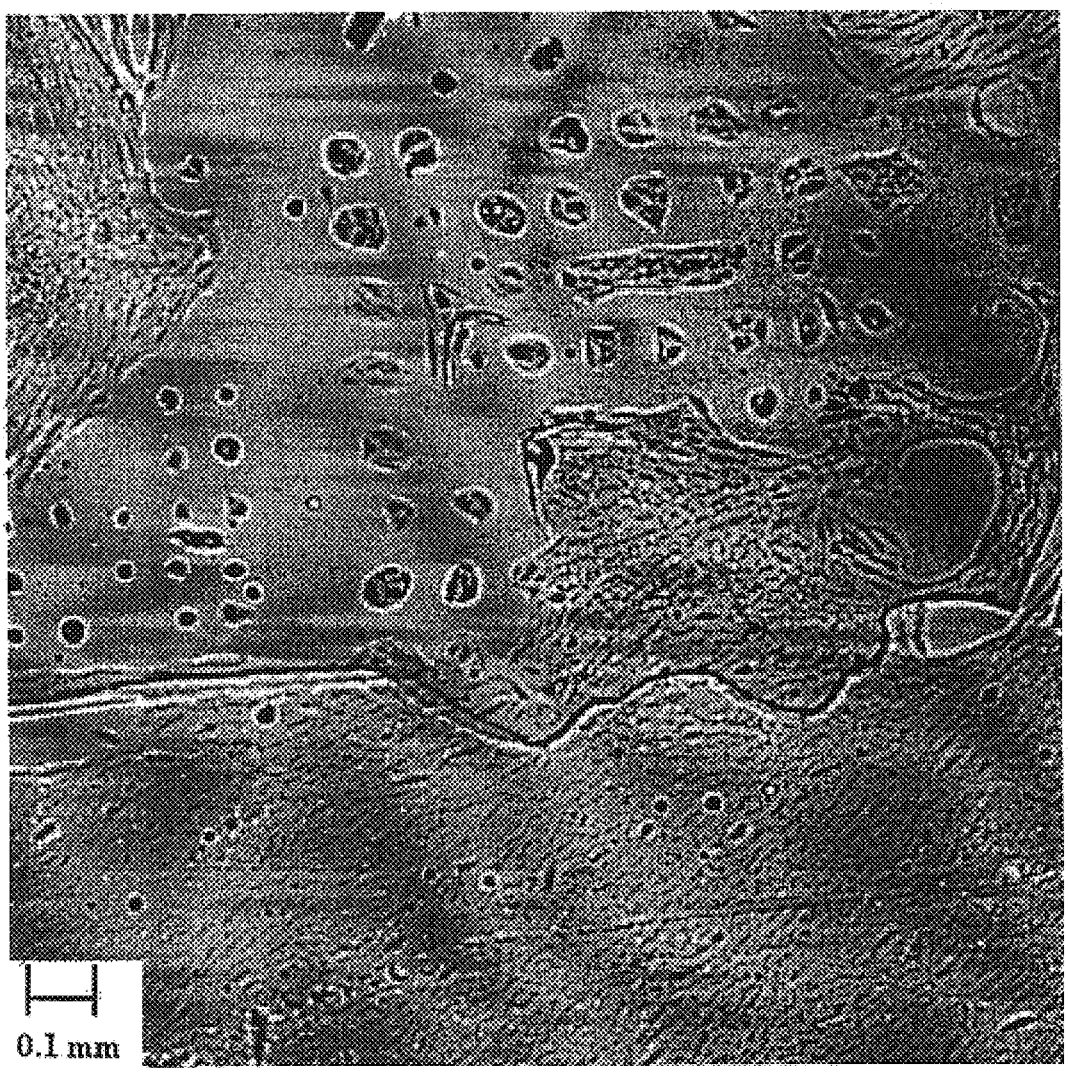
FIG. 5 illustrates a lens capsule micropatterned with the PDMS stamp illustrated in FIG. 4.

FIG. 5 is a SEM of a lens capsule that has received a micropattern of inhibitory molecules from the PDMS stamp illustrated in FIG. 4. The scale bar is 100 µm. It is evident that the cells are growing in a pattern determined by the micropattern deposited on lens capsule by stamp.

Tissues to be modified may be obtained by means known in the art, such as excision, biopsy, at surgery or at autopsy. As will be understood by those of ordinary skill in the art, care should be taken to avoid damage or contamination of the membranous tissue during procedures for obtaining it, as by following standard sterile operating procedures. It will be understood that the methods and apparatus are suitable for modifying any membranous tissue, including but not limited to ocular membranous tissue.

In the following discussion, methods and apparatus for modifying tissue will be discussed using primarily lens capsule tissue as exemplary membranous tissue. The methods and apparatus are thus also suitable for modifying inner limiting membrane tissues and other tissues, and may be used to modify inner limiting membrane and other tissues as well. The tissue modification provided by the methods of the invention is effective to alter the properties of the subject tissue to provide a more favorable substrate for cell attachment and growth, and to alter the physical and biochemical properties of the lens capsule tissue to allow more ready exchange of fluid and solutes across the tissue.

Membranous tissue such as lens capsule tissue and inner limiting membrane may be obtained from donor eyes, or from the patient (autologous tissue) by techniques known in the art, such as following lens extraction for cataract surgery. For example, lens capsule tissue may be obtained from an eye after a cataract incision has been made (either a scleral incision or a corneal incision). In this method, viscoelastic is next placed in the anterior chamber following making an incision. The viscoelastic is usually either Healon® (Pharmacia, Kalamazoo, Mich.) or Viscoat® (Alcon, Fort Worth, Tex.). The capsulotomy is then performed by using a cystotome needle. This needle is used to puncture the anterior capsule centrally, creating a capsule flap. This flap is then raised using the cystotome needle. Utrata forceps are used to grasp the flap of the capsule and it is pulled in a circular fashion. Pulling of the capsule for 360° in a controlled fashion will result in a round continuous capsulorhexis, exposing the cataract. The lens and lens capsule may then be removed.

Once removed, the membranous tissue (e.g., lens capsule, inner limiting membrane, or other eye tissue) may be maintained in vitro or prepared for in vivo transplantation. Membranous tissue is then placed on a glass, plastic, or polymer substrate. The glass substrate may be, for example, a glass cover slip. The plastic substrate may be, for example, a tissue culture dish. The polymer substrate, for example, may be a biodegradable polymer. Biodegradable polymer films may include poly-lactic acid, poly-glycolic acid, poly-lactic acid glycolic acid copolymers (PLGA), including PLGA (50:50 lactic to glycolic acid copolymer), poly-lactic acid polymers (PLLA), or polyethylene glycol/polylactic acid copolymer (PEG/PLA), polyorthoesters, polyanhydrides, polyphosphazines and blends and copolymers thereof. Methods for using biodegradable polymer films maybe found in, e.g., U.S. Pat. No. 5,512,600 to Mikos et al.

For example, the methods discussed in U.S. Pat. No. 5,512,600 and in *J. Biomedical Materials Research,* Vol 34:87–93 (1997) by Giordano et al. may be used to maintain healthy lens capsule, inner limiting membrane, or other membranous tissue in vitro and in vivo. Biodegradable (e.g., dissolvable after placement in an animal) polymer films comprising poly-lactic acid polymers (PLLA), poly-glycolic acid polymers, polyorthoesters, polyanhydrides, polyphosphazines, poly-lactic acid glycolic acid copolymers (PLGA), including PLGA (50:50 lactic to glycolic acid copolymer), and polyethylene glycol/polylactic acid copolymer (PEG/PLA) films may be placed on the bottom of plastic petri dishes. The lens capsule or other membranous tissue is then placed onto the surface and smoothed down with the use of a pipette. The membranous tissue and polymer film are transplanted together. The film dissolves in vivo leaving the membranous tissue behind. The film provides a greater ease of manipulation for the membranous tissue; for example, polymer films prevent lens capsule from curling, which is a problem observed with prior art methods. In addition, further treatment of the membranous tissue may be applied following these steps.

Lens capsule tissue (or other membranous tissue) may be placed in an environment suitable for cell growth, such as a tissue culture incubator or environmental chamber. In one embodiment, lens capsule tissue is immersed in a phosphate buffered saline solution (PBS) and maintained at 37° C. in a 95% $O_2$-5% $CO_2$ atmosphere. Following incubation, the PBS is removed with a sterile pipette and the lens capsule is allowed to lie flat on the bottom of a sterile petri dish. The lens capsule is then soaked in trypsin-EDTA for 1 hour to remove any lens epithelial cells and subsequently, penicillin/streptomycin for 30 minutes for sterility. The lens capsules are then rinsed three times in PBS followed by three rinses in distilled water. Each rinse is performed carefully with sterile pipettes. Finally, the lens capsule and the petri dish it rests on are sterilized under UV light for at least three hours.

In another embodiment, an interface chamber is used, wherein lens capsule tissue (or other membranous tissue) is placed on wetted filter paper covering a dish filled with phosphate buffered saline, and maintained at 37° C. in a 95% $O_2$-5% $CO_2$ atmosphere. It will be understood that various saline solutions known in the art, such as bicarbonate-buffered saline, or other saline solutions, may be substituted for PBS. Alternatively, culture medium (such as, for example, those as RPMI, DMEM or Hamm's F12 (Life Technologies, MD)) may be added to or may replace the saline in the methods, and growth factors, antibiotics, serum, and other materials may be added to the saline or culture medium used in maintaining lens capsule tissue.

Methods for modifying tissues include bulk modification methods and surface modification methods. Bulk modification methods include methods where substantial portions of the tissue, not limited to surface portions of the tissue, are modified by the method. Surface modification methods include methods wherein the tissue is modified at and near to the surface of the tissue, but is not greatly modified in other portions of the tissue.

The methods of the invention as applied to lens capsule tissue, whether bulk or surface modification methods, include removal of a lens capsule from an eye, flattening the lens capsule onto on a sterile glass or plastic substrate, such as a culture dish, microscope slide or a glass coverslip, that is submersed in phosphate buffered saline or other suitable solution, followed by further treatment of the lens capsule. It will be understood that similar treatments may be applied to inner limiting membrane tissue, or other membranous tissue from any organ.

Plastic substrates such as culture dishes and glass substrates such as microsope slides may be sterilized by standard procedures, such as by irradiation with ultraviolet light, immersion in acid followed by repeated washing in sterile distilled water, or other procedures known in the art. In addition, plastic or glass substrates may be used with or without surface coatings. Surface coatings may include collagen, collagen gel, fibronectin, laminin, a silane coating such as polymethyl silane, a polymer coating such as poly-L-lysine, or other coating known in the art.

In embodiments of the invention, the substrate is prepared for the membranous tissue. For example, tissue-culture plastic may be rinsed in a 70% ethanol solution to remove dust and oils and allowed to air dry. Following the drying step, the tissue culture plastic may be covered with a solution copmrising a desired extracellular matrix molecule (e.g., 4 mg/ml collagen, type I rat tail in PBS, 1 $\mu$g/ml laminin from human placenta in PBS, or 25 $\mu$g/ml fibronectin from human plasma in PBS) (collagen and fibronectin may be purchased from Sigma, St. Louis, Mo.). After one hour, the plastic may be rinsed in sterile distilled water twice and allowed to dry under UV overnight. If the lens capsule substrates are not immediately stamped, they are stored at 4° C.

Bulk modification methods for modifying membranous tissue such as lens capsule tissue include methods for modifying the thickness, permeability, and other properties of the lens capsule tissue. In one embodiment of the bulk modification method, such further treatment includes use of an excimer laser to ablate the surface of the lens capsule so that the overall thickness of the lens capsule is reduced. For example, the lens capsule may be ablated by a laser or ion beam, or by mechanical methods, so that the overall thickness mimics the thickness of Bruch's membrane.

A laser, such as an excimer laser (e.g., an argon fluoride laser (Lambda Physik, Model 201E)) may be used to provide pulses of laser light effective to ablate the surface of a lens capsule. For example, pulse of between about 10 to 20 ns duration, delivered at a frequency of about 1 to 50 Hz, with pulse energy densities of between about 300 to 500 millijoules per square centimeter (mj/cm$^2$) are effective to ablate the surface of a lens capsule in a desired manner. Each pulse is effective to ablate the tissue to a depth of between about 5 to 50 microns. Accordingly, repeated pulses are effective to reduce the thickness of the lens capsule tissue to a desired overall thickness. Methods as have been applied to the cornea may be followed or adapted and are suitable for use in photoablation of lens capsule tissue. Such methods of corneal photoablation are disclosed in, e.g., U.S. Pat. No. 4,665,913 to L'Esperance, U.S. Pat. No. 5,634,920 to Hohla, and U.S. Pat. No. 5,735,843 to Trokel.

In another embodiment of the bulk modification method, such further treatment following placement of tissue on a glass substrate includes use of a laser, such as, e.g., a YAG laser to produce micropores in the lens capsule. Such bulk modification by providing micropores alters the properties of the lens capsule tissue so as to provide a more favorable substrate for cell attachment and alters the biochemical properties of the lens capsule tissue to allow more ready exchange of fluid and solutes across the tissue. In embodiments of the invention, the micropores are sized on the order of 10 s of nanometers (nm) or less in diameter. Thus, micropores produced by the bulk modification methods may range in size between about 0.01 micron to about 10 microns, preferably between about 0.1 micron to about 1 microns. An erbium YAG laser can be used to provide pulses of between about 10 to 50 ns duration, at energy levels of between about 1 to 50 mj, preferably between about 1 to about 20 mj, effective to ablate holes in lens capsule tissue according to the methods of the invention.

In another embodiment of the bulk modification method, such further treatment following placement of membranous tissue on a glass substrate includes use of an ion beam to produce micropores in the lens capsule to provide a more favorable substrate for cell attachment and to allow more ready exchange of fluid and solutes across the tissue. See, for example, Goplani et al. *J Membr. Sci* 178:93–98 (2000), Xu et al., in *Material Research Society Symposium Proceeding* Vol. 540 "Microstructural Processes in Irradiated Materials ", pages 255–260 (1999), and Ohmichi et al., *J. Nuclear Materials* 248:354–359 (1997). In embodiments of the invention, the micropores are sized on the order of 10 s of nms to a few $\mu$m in diameter.

The membranous tissue may be freeze dried for purposes of exposing to the ion beams. Alternatively, the membranous tissue may be dried out entirely, then rehydrated after the micropores are made. An ion beam, such as a 120 MeV beam of Si$^{28}$ ions, may be used to irradiate the tissues. Following exposure to the ion beam, the membranous tissues may be rehydrated. Biological etching using collagenase and other proteases or proteolytic enzymes, as discussed below, may be used to enlarge the microholes if larger holes are desired.

In another embodiment of the bulk modification method, treatment of the membranous tissue includes deposition of proteolytic enzymes onto the membranous tissue effective to biologically etch the surface and interior of the membranous tissue to provide desired topology and surface adhesion properties to the tissue. In some embodiments of this method, the deposition step includes contacting the lens capsule or other membranous tissue with a microcontact printing stamp carrying enzymes effective to biologically etch the surface and interior of the tissue. After stamping of the enzymes onto the tissue, albumin or an enzyme inhibitor may be used to stop the reaction after a given time. For example, incubation with collagenase is preferentially carried out for various periods up to 26 h at 20° C. in a constant temperature water bath, and the collagenase reaction stopped by the addition of EDTA to a final concentration of 50 mM. Incubation with trypsin (e.g., 0.25% trypsin in a balanced salt solution without calcium or magnesium) may be performed at about 0 to 5° C. for about 6 to about 18 hours. Following this incubation with trypsin, the trypsin solution may be removed and the membranous tissue incubated at 37° C. for 20 to 30 minutes before washing with a wash solution containing divalent cations (such as calcium and magnesium) in the amount of about 1 to about 5 mM (and optionally containing a trypsin inhibitor such as soybean trypsin inhibitor). Alternatively, membranous tissues may be incubated with dispase (about 0.5 to about 3 U/ml) or other proteolytic enzymes in a balanced salt solution that is substantially divalent cation-free at 37° C. for up to several hours before removal of the solution and washing of the membranous tissue with a balanced salt solution containing about 1 to about 5 mM divalent cations.

In embodiments of the bulk modification methods, for example, agents such as collagenase, trypsin, chymotryptsin, dispase, liberase, thermolysin, pepsin, papain, and other proteases may be applied as solutions in distilled water, phosphate-buffered saline, or other buffered solution, at concentrations ranging between about 0.01 mg/mL to about 100 mg/mL, preferably between about 1 mg/mL to about 20 mg/mL, to the surface of a microcontact printing stamp. The surface of the tissue, such as lens capsule tissue, may be contacted in air or while immersed in a saline solution. Where the protease is active in the absence of calcium, such as for trypsin, chelating agents such as EDTA and EGTA, preferably at concentrations in the range of between about 1 to about 10 mM, may be included in the solutions. In such cases, enzymatic action may be halted when desired by the addition of calcium and or magnesium to the solution. In any case, enzymatic action may be stopped by dilution with excess of enzyme-free solution or by addition of an appropriate enzyme inhibitor. (For example, trypsin may be inhibited by a trypsin inhibitor such as soybean trypsin inhibitor (T-9003, Sigma Chemical Co. St. Louis, Mo.).)

In another embodiment of the bulk modification method, treatment of inner limiting membrane or lens capsule tissue includes impregnation of the tissue with a deactivated enzyme, such as a deactivated collagenase enzyme, that is activated by laser light illumination. For example, in one embodiment very small regions sized less than a micron in diameter of tissue are activated by illumination with a 2-photon confocal laser system. Enzymes activated in this way are effective to degrade or otherwise alter tissue in the small region where activation occurs, while nearby regions not activated by the confocal laser system remain unaltered. The activated enzyme may be flushed out or deactivated by water. Enzymes suitable for the practice of the invention include but are not limited to collagenase, trypsin, chymotrypsin, dispase, liberase, papain, pepsin, thermolysin, and other proteases.

In one embodiment of the surface modification method, microcontact printing techniques are used to fabricate chemical micropatterns of biomolecules onto tissue. For example, surface modification of lens capsule tissue may include deposition of patterns of biomolecules onto lens capsule tissue. Such patterns may include repeated iterations of geometric or linear patterns, or may include only a few, or a single, pattern not made up of smaller pattern units. Thus, patterns of surface modification may include linear arrays of biomolecules deposited onto a tissue surface, or curved arrangements of biomolecules, series of circularly-shaped patterns, such as rings or dots, of biomolecules, or a series of other shapes, including multiple shapes in a single pattern, of biomolecules. Alternatively, such patterns may include extended areas substantially covered by deposited biomolecules, or extended areas substantially devoid of deposited biomolecules. It will be understood that the methods include any suitable pattern comprising lines, shapes, or regions of deposited molecules, including regions devoid of deposited molecules situated between regions with deposited biomolecules. Such micropatterns may, in general improve cell attachment and growth on the modified membranous surface. However, in embodiments of the invention, micropatterns are produces where regions of the modified membranous tissue are rendered less suitable, or unsuitable, for cell attachment and growth. In this way, cell attachment and growth may be directed to and limited to those regions of the membranous tissue that have not been so treated.

Microcontact printing stamps may include the entire pattern to be deposited onto target tissue, or may include a portion of the desired pattern. Where the stamp includes a portion of the desired pattern, multiple applications of the microcontact printing stamp to the tissue surface are effective to provide a desired pattern of biomolecules on the tissue surface. Where the stamp includes the entire pattern, biomolecules may be deposited onto the microcontact printing stamp itself in the desired pattern.

The patterns of biomolecules on a microcontact printing stamp may be determined by directed placement of the biomolecules on the stamp, or may be determined by the surface geometry of the stamp. Where the pattern of biomolecules is determined by the surface geometry of the stamp, the geometric pattern may include locally-raised ridges, where contact of the stamp with a source of biomolecules is effective to deposit such biomolecules onto the raised surfaces, with substantially no biomolecules being deposited on other, non-raised portions of the surface. In such a microcontact stamp, the pattern of biomolecules deposited onto a tissue would follow the pattern of the raised surfaces Alternatively, the pattern may include depressions, valleys or fissures, such as scratches made into a surface, where contact of the stamp with a source of biomolecules is effective to deposit such biomolecules onto a major portion of the surface, with substantially no biomolecules being deposited on the depressed portions of the surface. In such a microcontact stamp with depressions, biomolecules would be deposited over a substantial portion of the tissue, with regions substantially lacking deposited biomolecules following the pattern of the depressed surfaces.

In some embodiments of this method, the patterns are sized on the order of a few microns or less. Accordingly, in embodiments of the surface modification methods of the invention, the individual patterns of which the overall patterns are comprised may range in size between about 0.1 micron to about 20 microns, preferably between about 0.5 microns to about 5 microns.

Biomolecules suitable for deposition onto tissue surface include proteins, peptides, organic molecules, oligosaccharides, and small chain polymers, including but not limited to collagen, hyaluronic acid, keratin sulfate, glycosaminoglycan, methylacrylate, poly (methyl methacrylate), polystyrene, poly(methyl styrene), polylysine, polylactic glycolic acid (PLGA)-derivatized polylysine, polylysine peptides, and silane polymers such as octadecyltrichlorosilane (OTS). Surface modification comprising deposition of biomolecules is effective to alter biological properties of the tissue, such as the ability or ease of attachment by cells placed onto microfabricated tissues. For example, deposition of hydrophobic molecules is effective to deactivate selective cell attachment sites on lens capsule tissue.

Microcontact printing stamps may be made of any material capable of retaining a suitable pattern, such as glass, ceramic, metal, plastic, polymer, or other material. In presently preferred embodiments of the method, microcontact printing stamps include poly(dimethylsiloxane) (PDMS). Microcontact printing stamps may be cast in PDMS from masters containing desired patterns, such as, for example, a grid pattern of lines. Alternatively, where the pattern to be formed is determined by the pattern of deposition of biomolecules onto a tissue, the stamp may include a simple surface, such as a flat surface, suitable for carrying biomolecules. Such stamps may include pins, slotted pins, bars or rods, for example, and may have circular, triangular, square, rectangular, other polygonal or irregularly shaped perimeters.

In embodiments of the surface modification method, the surface of the lens capsule tissue is masked to cover part, but not all, of the surface of the lens capsule tissue, and then irradiated with ultraviolet (UV) radiation effective to denature the extracellular matrix (ECM) of the exposed portions of tissue. This deactivates molecules specific for cell adhesion, and to inhibits or prevents cell adhesion and growth in the exposed, but not the covered, regions. Thus, in this embodiment of the methods of the invention, portions of the substrate are rendered unsuitable for cell attachment and growth. In this way, growing cells can be directed to desired regions, and away from undesired regions.

In embodiments of the invention, the entire substrate surface may be deactivated to prevent attachment or growth of cells, and then specific regions reactivated. By deactivating proteins that are specific for cellular adhesion, the growth of cells may be limited to confined regions. A deactivating substance is one that prevents the attachment, the spread, or both, of growing cells. For example, 0.2% polyvinyl alcohol (PVA) solution and mucilage are effective deactivating substances.

A surface may be deactivated, and a portion of that surface reactivated, by application of a deactivating substance to the surface. For example, 0.2% PVA applied to the surface of the lens capsule is effective to deactivate the surface of the lens capsule. Exposure of the deactivated lens capsule surface to a micropattern of light from an excimer laser is effective to ablate a micropattern on the lens capsule surface. For example, a micropattern may be produced on the lens capsule surface by illumination of the lens capsule surface through an irradiation mask. The ablated micropattern, by removing or altering the deactivating substance, reactivates portions of the substrate to allow cell growth and spreading into the ablated regions, thereby directing cell growth to follow a desired pattern.

The masking step may include placement of a grid onto the tissue, where the grid includes a material effective to prevent irradiation of the surface by a source of radiation, such as UV radiation. The grid may be made of materials including metal, glass, plastic, ceramic, polymer, protein, or other material effective to absorb or reflect UV radiation.

In an alternative embodiment of the masking method, the masking step includes using microcontact printing techniques to apply a pattern of protecting molecules onto the surface of the lens capsule tissue effective to prevent ECM denaturation in regions covered by the protecting molecules. Thus, the grid of a masking step may include a coating on the surface effective to screen the surface from irradiation. Such a coating may include a protein, preferably one rich in tyrosine and other amino acid residues that absorb ultraviolet light, a polymer effective to absorb UV light, or a small molecule effective to screen UV light, such as, for example, para-amino benzoic acid (PABA).

It will be understood by one of skill in the art that surface modification methods and bulk modification methods may each be applied to a single tissue. Thus, for example, the same lens capsule tissue may be treated with both surface modification and bulk modification methods effective to provide microfabricated lens capsule tissue.

Microfabricated tissues are suitable substrates for growing cells. A method for growing cells on microfabricated tissues includes providing a microfabricated tissue produced by one of the methods described above, and applying cells to the microfabricated tissue. For example, the microfabricated tissue may include a microfabricated lens capsule with a pattern on its surface, such as a pattern of collagen, and the cells may include IPE or RPE cells. In preferred embodiments of the invention comprising autologous tissue and cells, the microfabricated tissues and the cells are obtained from the same animal.

The invention also provides methods for using microfabricated tissues, comprising surgical methods for transplanting microfabricated tissues into an animal. In preferred embodiments, the methods for transplanting microfabricated tissues into an animal include surgical methods for transplanting microfabricated tissues into the eye of an animal. In most preferred methods, the transplantation of microfabricated tissues into the eye of an animal includes transplantation of microfabricated lens capsule tissue near to or into the retina of an animal. In some embodiments, the transplanted tissue further includes cells grown on microfabricated lens capsule tissues. In other embodiments, the transplanted tissue includes RPE or IPE cells grown on microfabricated lens capsule tissues. Alternatively, dissolvable polymer substrates may be used for growing cells for transplantation. In further embodiments, the transplanted tissue includes RPE or IPE cells grown on microfabricated membranous tissues or on dissolvable polymer substrates, where the cells and tissues are taken from the same animal as the animal into which they are transplanted (autologous tissue).

Methods for isolating or removing RPE cells from an eye may be found in Pfeffer, B. A., Chapter 10, "Improved Methodology for Cell Culture of Human and Monkey Retinal Pigment Epithelium," *Progress in Retinal Research,* Vol. 10 (1991) Ed. Osborn, N., and Chader, J.; these methods may also be applied to IPE cells. The cells may be removed from a donor eye, or from the intact eye of a patient, including the eye that will ultimately receive a transplant of microfabricated tissue with cells. Methods for harvesting cells obtained in a biopsy, as for an autologous transplantation procedure, may be found in Lane, C., et al. *Eye* 3:27–32 (1989). Further methods for procurement of RPE and IPE may be found, e.g., in Abe et al., 1999, Thumann, et al., 1999; Lappas et al., 2000; and in Thurmann et al., 2000.

The IPE or RPE cells may be dispersed in saline, such as phosphatebuffered saline, at a density of between about $10^4$ cells/mL to about $10^7$ cells/mL. Isolated RPE or IPE cells may be applied to microfabricated tissue, for example, to microfabricated lens capsule tissue by gently pipetting a solution containing IPE or RPE cells onto the microfabricated tissue immersed in PBS, followed by maintenance of the cells and tissue at 37° C. in a sterile 95% $O_2$-5% $CO_2$ atmosphere for 12 hours. The PBS may be removed with a sterile pipette and the lens capsule allowed to lie flat on the bottom of a sterile petri dish or other container. The lens capsule may then be soaked in trypsin-EDTA for 1 hour to remove any lens epithelial cells and subsequently, penicillin/streptomycin for 30 minutes for sterility. Following this, the lens capsules may then be rinsed three times in PBS followed by three rinses in distilled water. Each rinse should be performed carefully with sterile pipettes. Finally, the lens capsule and its support are sterilized under UV light for at least three hours.

Transplantation of microfabricated lens capsule tissue into the subretinal space may be effected by any means providing access to the subretinal space. Access to the subretinal space may be provided, for example, by a scleral incision placed laterally on the eye, or via the vitreous humor by a more frontal incision. Procedures providing access to, and transplantation into, the retina, including the subretinal space, have been described; see, for example, Abe et al., *Tohoku J. Exp. Med.* 189:295–305 (1999), Abe et al., *Tohoku J. Exp. Med.* 191:7–20 (2000), Lappas et al., *Graefes's Arch Clin Exp Ophthalmol.* 238:631–641 (2000), Thumann, et al., *Arch. Ophthalmol.* 118:1350–1355 (2000), U.S. Pat. No. 5,962,027 to Hughes and U.S. Pat. No. 6,045,791 to Liu.

EXAMPLE 1

Microcontact printing was used to deposit micron-sized patterns of biomolecules onto lens capsule tissue. Poly(dimethyl siloxane) (PDMS) stamps were cast from masters containing a topological pattern of grid lines spaced 50 microns apart. The PDMS stamp was made from a master that was microfabricated from a silicon wafer. PDMS stamps were used to microfabricate patterns onto lens capsule tissue. Shown in FIG. 2 is a scanning electron micrograph (SEM) of a PDMS stamp used to deposit a micropattern onto a piece of human lens capsule tissue.

The PDMS stamp shown in FIG. 2 has a surface topology given by an array of lines. The line-shaped relief pattern is collated with poly-L-lysine that is transferred to the lens capsule. Each line is separated by approximately 50 µm.

FIG. 3 shows a human lens capsule stamped with the PDMS stamp shown in FIG. 2. The PDMS stamp was used to deposit square patterns of poly-L-lysine onto the lens capsule. This example shows that the stamp is effective to produce a pattern on a surface corresponding to the pattern of the stamp.

EXAMPLE 2

A SEM of a PDMS stamp with circular patterns used for micropatterning tissue is shown in FIG. 4. As shown, the stamp has a surface topology given by an array of circular wells of approximately 50 µm in diameter. When the relief pattern is coated with an inhibitory molecule, such as PVA or mucilage, and the stamp applied to a lens capsule, the inhibitory molecules are transferred to the lens capsule in the pattern shown. FIG. 4 shows the surface of a lens capsule that has been patterned with the PDMS stamp shown in FIG. 4. This example shows that the stamp is effective to place a pattern on the lens capsule surface that corresponds to the pattern of the stamp.

Thus, application of the stamps of the invention are able to deposit inhibitory molecules everywhere but on the circles themselves, thus allowing the cells to attach only on these areas. Because the lens capsule actively allows growth, inhibitory patterns are required for patterned growth. Use of the stamp on substrates treated to inhibit growth would require the use of activating molecules to pattern growth on the substrate.

EXAMPLE 3

Masking of the surface of lens capsule tissue and then irradiating the exposed surface, but not the masked surface, with UV radiation is accomplished by placement of a SEM grid onto the surface of lens capsule tissue. A SEM grid with spacing of 50 microns is placed onto the exposed surface of an excised lens capsule tissue resting on a glass coverslip immersed in phosphate-buffered saline. The surface of the lens capsule tissue and the SEM grid are not immersed in the phosphate-buffered saline, but rise above the level of the phosphate-buffered saline. UV light is directed onto the exposed surface of the lens capsule tissue effective to irradiate the lens capsule tissue not resting immediately below the SEM grid material. After irradiation, the SEM grid is removed. The lens capsule surface includes a micropattern of lines comprising tissue not irradiated (regions under SEM grid material) enclosing regions comprising irradiated tissue.

EXAMPLE 4

One therapy for AMD is to transplant suspensions of either retinal pigment epithelial (RPE) cells or iris pigment epithelial (IPE) cells to rescue the diseased retina. The present invention provides novel tissue engineering techniques to precision engineer autologous human tissues as a substrate for transplanting cells, such as IPE and RPE cells. Suitable tissues include membranous tissues, such as lens capsule and inner limiting membrane tissue (e.g., human lens capsule).

A microgeometry of inhibitory molecules is arranged onto the surface of a suitable substrate. Suitable substrates include human lens capsule, collagen gel, collagen-, fibronectin-, and laminin-coated plastic, and a dissolvable polymer such as PLGA or PLLA. Human lens capsules may be obtained during cataract surgery. Cultures of experimental RPE cells are grown on these microengineered surfaces and analyzed using scanning electron microscopy, atomic force microscopy, and fluorescence microscopy. Comparisons between microfabricated surfaces of autologous tissue and synthetic surfaces and membranes are then made.

The comparisons demonstrate that individual RPE cells may be directed to grow in microenvironments on the respective biological surfaces.

What is claimed is:

1. An ocular implant comprising a bioasorbable substrate, a microfabricated membranous tissue layer secured to the substrate and cells on the surface of the microfabricated membranous tissue layer, said cells separated into regions on said surface by creating a pattern on said surface enclosing said regions for receiving cells.

2. The implant of claim 1, wherein the tissue of the membranous tissue layer is selected from the group consisting of lens capsule, inner limiting membrane, and non-ocular membranous tissue.

3. The ocular implant of claim 1 wherein the cells are cells selected from the group consisting of IPE cells and RPE cells.

4. The ocular implant of claim 1 wherein the cells on the microfabricated tissue layer are separated by growth inhibitory barriers.

5. The ocular implant of claim 1 wherein the substrate is formed of a material selected from the group consisting of poly-lactic acid, polyglycolic acid, polyorthoesters, polyanhydrides, polyphosphazines, poly-lactic acid glycolic acid copolymers, polyethylene glycol/polylactic acid copolymers and blends and copolymers thereof.

6. The ocular implant of claim 1 wherein the membranous tissue layer is about 2 to about 5 micrometers in thickness.

7. The ocular implant of claim 1 wherein the membranous tissue layer has micropores or pits.

8. The ocular implant of claim 1 wherein the membranous tissue layer has a micropattern of biomolecules.

9. The ocular implant of claim 8 wherein the biomolecules of the micropattern of the membranous tissue layer are selected from the group consisting of proteins, peptides, organic molecules, oligosaccharides, and small chain polymers.

10. The ocular implant of claim 8 wherein one or more of the biomolecules of the micropattern of the membranous tissue layer are selected from the group consisting of poly (methyl methacrylate), polystyrene, poly (methyl styrene), collagen, keratin sulfate, hyaluronic acid, glycosaminoglycan, octadecyltrichlorosilane, silane polymers, polylysine, polylactic glycolic acid (PLGA)-derivatized polylysine and polylysine peptides.

11. An implant comprising a polymeric substrate, a membranous tissue layer secured to the substrate and an array of cells on the surface of the membranous tissue, wherein said cells are separated into regions on said surface defining said array by creating a pattern on said surface enclosing said regions for receiving cells.

12. The implant of claim 11 wherein the cells on the tissue layer are in a predetermined pattern as depicted in FIG. 3 or FIG. 5.

13. The implant of claim 11 wherein the substrate is formed of a material selected from the group consisting of poly-lactic acid, polyglycolic acid, polyorthoesters, polyanhydrides, polyphosphazines, poly-lactic acid glycolic acid copolymers, polyethylene glycol/polylactic acid copolymers and blends and copolymers thereof.

14. The implant of claim 11 wherein the membranous tissue layer is about 2 to about 5 micrometers in thickness.

15. The implant of claim 11 wherein the membranous tissue layer has micropores or pits.

16. The implant of claim 11 wherein the membranous tissue layer has a micropattern of biomolecules.

17. The implant of claim 16 wherein the biomolecules of the micropattern of the membranous tissue layer are selected from the group consisting of proteins, peptides, organic molecules, oligosaccharides, and small chain polymers.

18. The implant of claim 17 wherein one or more of the biomolecules of the micropattern of the membranous tissue layer are selected from the group consisting of poly (methyl methacrylate), polystyrene, poly (methyl styrene), collagen, keratin sulfate, hyaluronic acid, glycosaminoglycan, octadecyltrichlorosilane, silane polymers, polylysine, polylactic glycolic acid (PLGA)-derivatized polylysine and polylysine peptides.

* * * * *

UNITED STATES PATENT AND TRADEMARK OFFICE
CERTIFICATE OF CORRECTION

PATENT NO.   : 6,939,378 B2
DATED         : September 6, 2005
INVENTOR(S)  : Fishman et al.

It is certified that error appears in the above-identified patent and that said Letters Patent is hereby corrected as shown below:

Column 18,
Line 46, before "substrate" delete "bioasorbable" and insert -- bioabsorbable --.

Column 20,
Line 18, delete "17" and insert -- 16 --.

Signed and Sealed this

Seventeenth Day of January, 2006

JON W. DUDAS
*Director of the United States Patent and Trademark Office*